United States Patent
Yang et al.

[11] Patent Number: 5,889,282
[45] Date of Patent: Mar. 30, 1999

[54] ANALYTICAL METHOD OF AUGER ELECTRON SPECTROSCOPY FOR INSULATING SAMPLE

[75] Inventors: Hee Seok Yang, Seoul; Taek Jin Lim; Jae Sung Han, both of Kyungki-do, all of Rep. of Korea

[73] Assignee: Samsung Electronics Co., Ltd., Suwon, Rep. of Korea

[21] Appl. No.: 919,154

[22] Filed: Aug. 28, 1997

[30]    Foreign Application Priority Data

Sep. 17, 1996  [KR]    Rep. of Korea ........................ 96-40446

[51] Int. Cl.$^6$ ..................................................... H01J 37/00
[52] U.S. Cl. ............................................ 250/305; 250/307
[58] Field of Search ..................... 250/305, 306, 250/307

[56]              References Cited

U.S. PATENT DOCUMENTS 4,563,368   1/1986   Tihanyi et al. ........................... 427/82
4,992,661   2/1991   Tamura et al. ........................... 250/309
5,510,614   4/1996   Mitsuya et al. .......................... 250/307

*Primary Examiner*—Bruce Anderson
*Attorney, Agent, or Firm*—Jones & Volentine, L.L.P.

[57]              ABSTRACT

A method of Auger Electron Spectroscopic (AES) analysis for a surface of an insulating sample. The method is characterized by performing an AES analysis after depositing a conductive layer of a designated thickness on the surface of a sample containing an insulating layer by means of an ion beam sputtering for the purpose of the preventing charge accumulation. The conductive layer preferably is deposited to have a thickness of at least 6 Å to 50 Å and a beam voltage used for applying the conductive layer is at least 3 Kev. The conductive layer is made of any of iridium(Ir), chrome(Cr) and gold(Au). Because any electron charge generated on the sample is discharged via the conductive layer, the AES analysis can be performed for a sample containing an insulating layer.

9 Claims, 8 Drawing Sheets

ANALYTICAL METHOD OF AUGER ELECTRON SPECTROSCOPY FOR INSULATING SAMPLE

BACKGROUND OF THE INVENTION

1. Field of the Invention

The present invention relates to an analytical method of Auger Electron Spectroscopy (hereinafter referred to "AES") for a sample having an insulating layer, and more particularly, to an analytical method of Auger Electron Spectroscopy for an insulating sample for which charge accumulation effects are prevented.

2. Background of the Related Art

In general, semiconductor devices include various elements such as memories, LCD's and the like. Normally a number of analyses are performed for a sample, which was produced in the course of the fabrication of the semiconductor device, for the purpose of increasing yields and enhancing performance.

One typical analytical apparatus for such purposes is an Auger Electron Spectroscopy (AES) system that is used to analyze contamination or composition of the surface and depth of a sample's layers. AES analyzes the elements in a sample by shooting an electron beam onto a selected atom on the surface of the sample and scanning the kinetic energy of an auger electron resulting from the impact of the electron beam. Due to its excellent analytical performance on minute areas, AES is chiefly used to analyze the particles on the surface of a wafer, damaged parts of a semiconductor structure, and the composition of thin layers, e.g., $Si_3N_4$, $WSi_2$, TiN, PSG, or BPSG. In particular, AES is characterized by its high resolution due to the application of the electron beam.

A conventional AES system is incapable of analyzing an insulating layer through the use of an electron beam because of the charge accumulation effect of the insulating layer. Thus, the analysis is limited to a conductive sample that does not experience a charging effect.

The AES analysis may be performed using a method of depositing conductive materials such as gold on a sample for a scanning electron microscopic analysis. However, with a device such as a diode sputtering apparatus that is used for a general deposition, it is not easy to deposit a conductive layer with a thickness of less than 100 Å to 150 Å, or to regulate the deposited layer to have a precise thickness of a desired level. When using an AES system that is restricted to operating with a conductive layer of about 30 Å to 50 Å in thickness, it is therefore impossible to perform an analysis for the surface of a sample on which a conductive layer of at least 100 Å to 150 Å in thickness was deposited.

SUMMARY OF THE INVENTION

The present invention provides a method of AES analysis for an insulating layer that substantially overcomes one or more of the problems due to the limitations and disadvantages of the conventional art.

To achieve these and other objects and advantages, and in accordance with the purpose of the present invention, a quantitative and qualitative AES method of analysis for the surface of an insulating sample is characterized by performing an AES analysis after depositing a conductive layer of a designated thickness on the surface of a sample containing an insulating layer for the purpose of preventing charge accumulation effects.

The conductive layer is preferably deposited with a thickness of at least 6 Å to 50 Å and the beam applied is at least 3Kev. The resulting conductive layer is optionally made of any of iridium(Ir), chrome(Cr) and gold(Au). Preferably, the conductive layer is deposited by means of ion beam sputtering. Because any electric charge generated on the sample is discharged via the conductive layer, the AES analysis can be performed for the sample containing an insulating layer.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings illustrate embodiments of the invention, in which.

DETAILED DESCRIPTION OF THE PREFERRED EMBODIMENT

Reference will now be made in detail to the preferred embodiments of the present invention, examples of which are illustrated in the accompanying drawings. Although the invention can be used in a wide variety of insulating layer applications, it is described herein with regard to sputtering and analysis performed for the glass which is used for a LCD. However, the discussion below is not meant to be limited to the embodiments disclosed.

Figure 1:
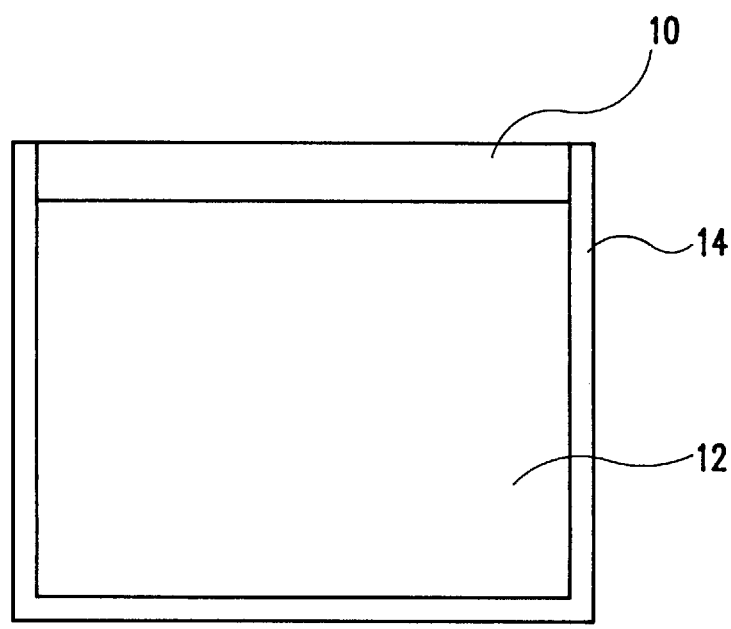
FIG. 1 is a sectional view of an insulating sample with a conductive layer coated thereon for use in the method of the present invention.

The embodiment of the present invention is a technique for analyzing an insulating sample by coating the sample 10 with an iridium layer 12 as shown in FIG. 1. Normally, shooting an electron beam on the insulting sample 10 for the purpose of an AES analysis causes a charge to accumulate. Thus, the iridium 12 is formed by means of ion beam sputtering to provide the sample 10 with a conductive iridium layer. When the sample 10 is arranged with the iridium layer 12 on a fixing device (not shown) of the AES system, the side walls and the lower part of the sample and iridium layer 12 are taped with an aluminum tape 14 to fix them in place. Then, any electric charge that would normally accumulate is discharged via the conductive iridium layer 12, the aluminum tape 14 and the fixing device, thereby preventing charge accumulation during the AES analysis. SEC.181

With a customary ion beam sputtering process, the thickness of a layer to be deposited can be regulated within a range of several Å. Accordingly, if process conditions for an iridium target using an ion beam sputtering device are established for depositing a layer to have a thickness of 7 Å, one could expect an iridium layer 12 of about 7 Å in thickness to be coated on the sample 10. Thinner conductive layers are preferred in an AES analysis because much more analytical depth can be secured, but the layer should be at least thick enough not to allow charge accumulation.

Regarding the relationship between the electron beam voltage and the sample, as the beam voltage increase, the analytical depth is greater and the coated conductive layer affects the results less. Furthermore, the AES should be established to have a minimum beam current because charge accumulation occurs in proportion to the current.

Experimental results concerning the correlation of the thickness of a layer coated on the sample and the beam voltage, along with the correlation to charge accumulation are shown in Table 1 below and FIG. 2 through FIG. 8. In this experiment, the beam current was not significant.

Figure 2:
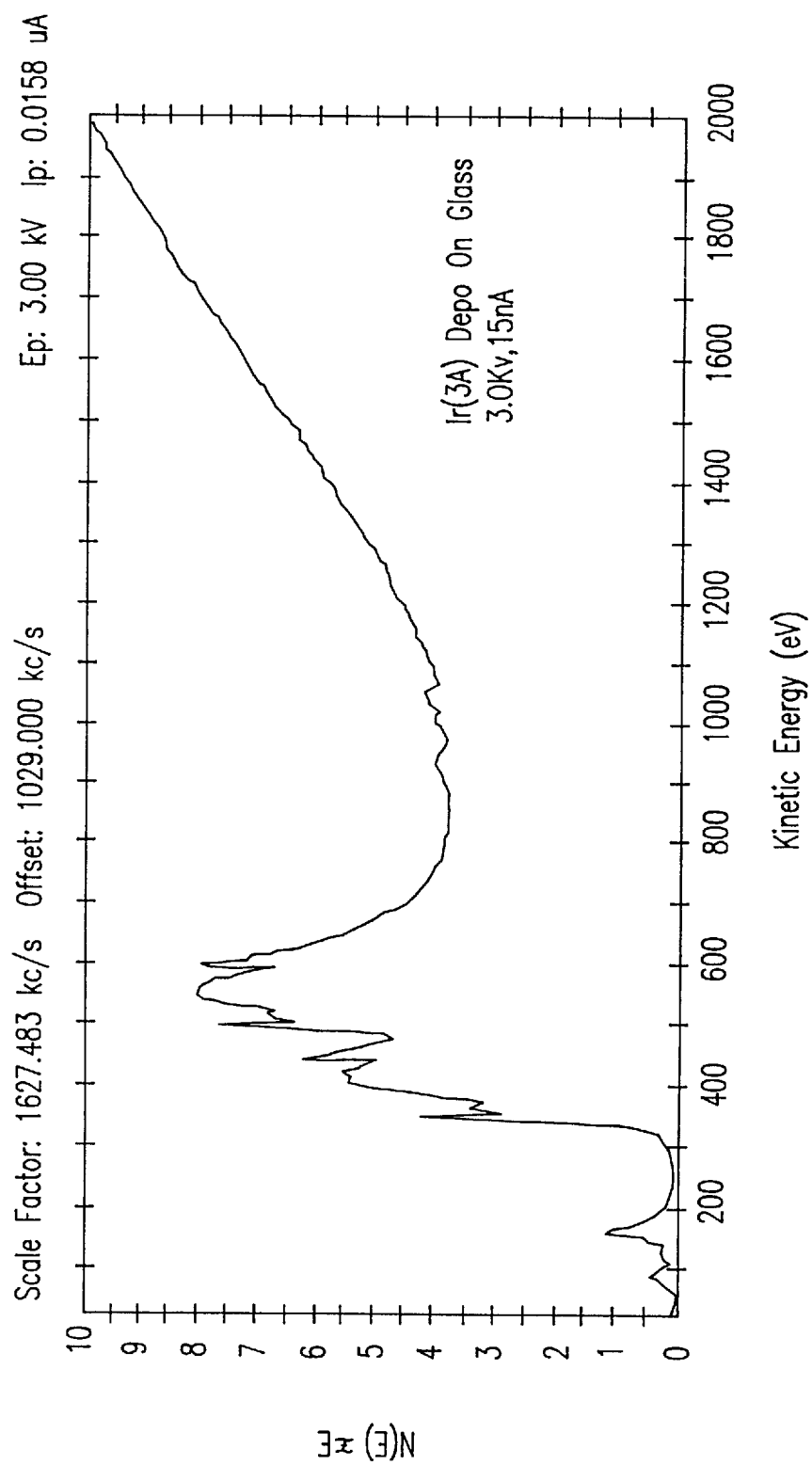
FIG. 2 is a graph of an AES analysis where an iridium layer formed on glass has a thickness of 3 Å and uses a beam voltage of 3 KV.
Figure 3:
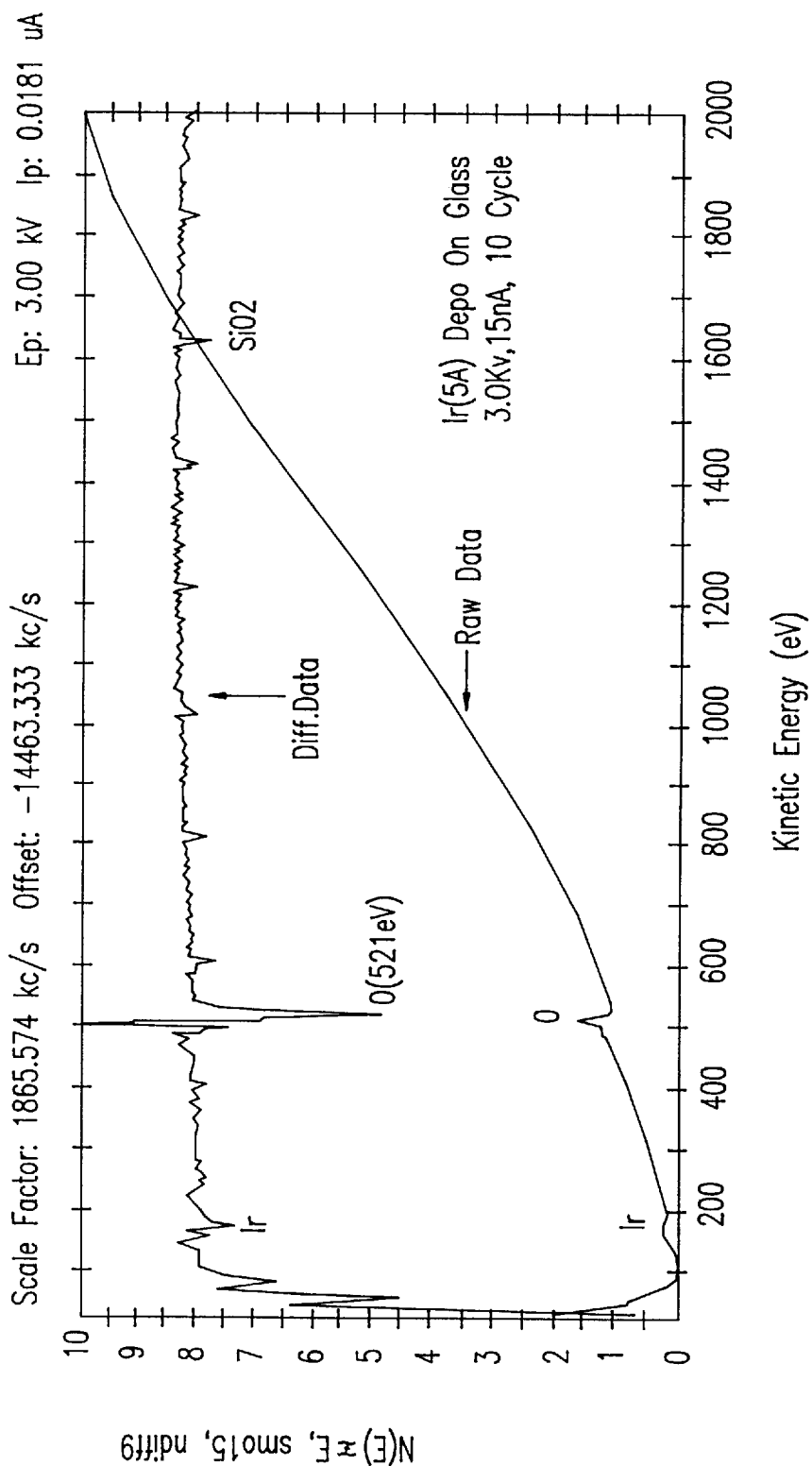
FIG. 3 is a graph of an AES analysis where an iridium layer formed on glass has a thickness of 5 Å and uses a beam voltage of 3 KV.
Figure 4:
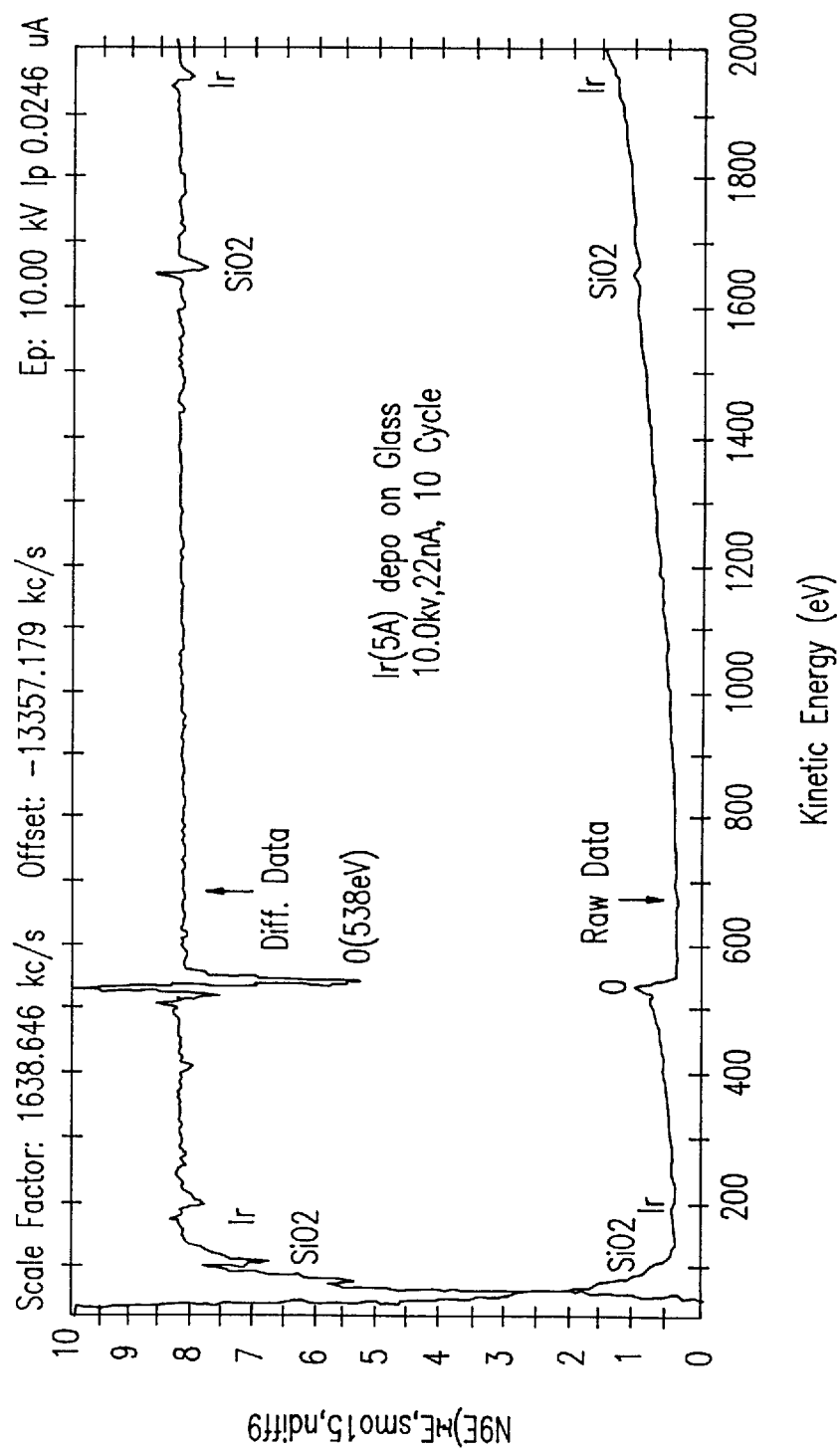
FIG. 4 is a graph of an AES analysis where an iridium layer formed on glass has a thickness of 5 Å and uses a beam voltage of 10 KV.
Figure 5:
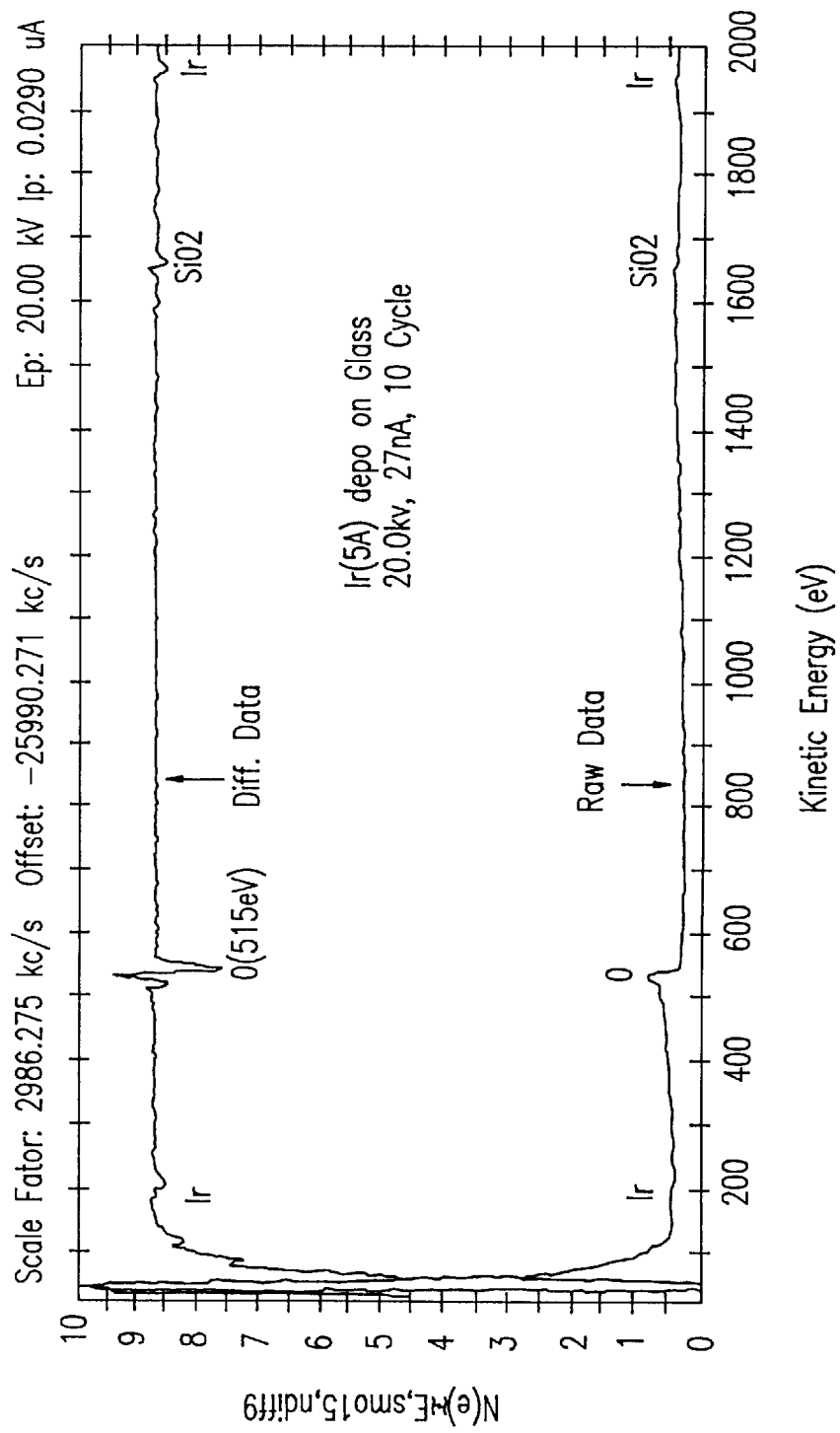
FIG. 5 is a graph of an AES analysis where an iridium layer formed on glass has a thickness of 5 Å and uses a beam voltage of 20 KV.
Figure 6:
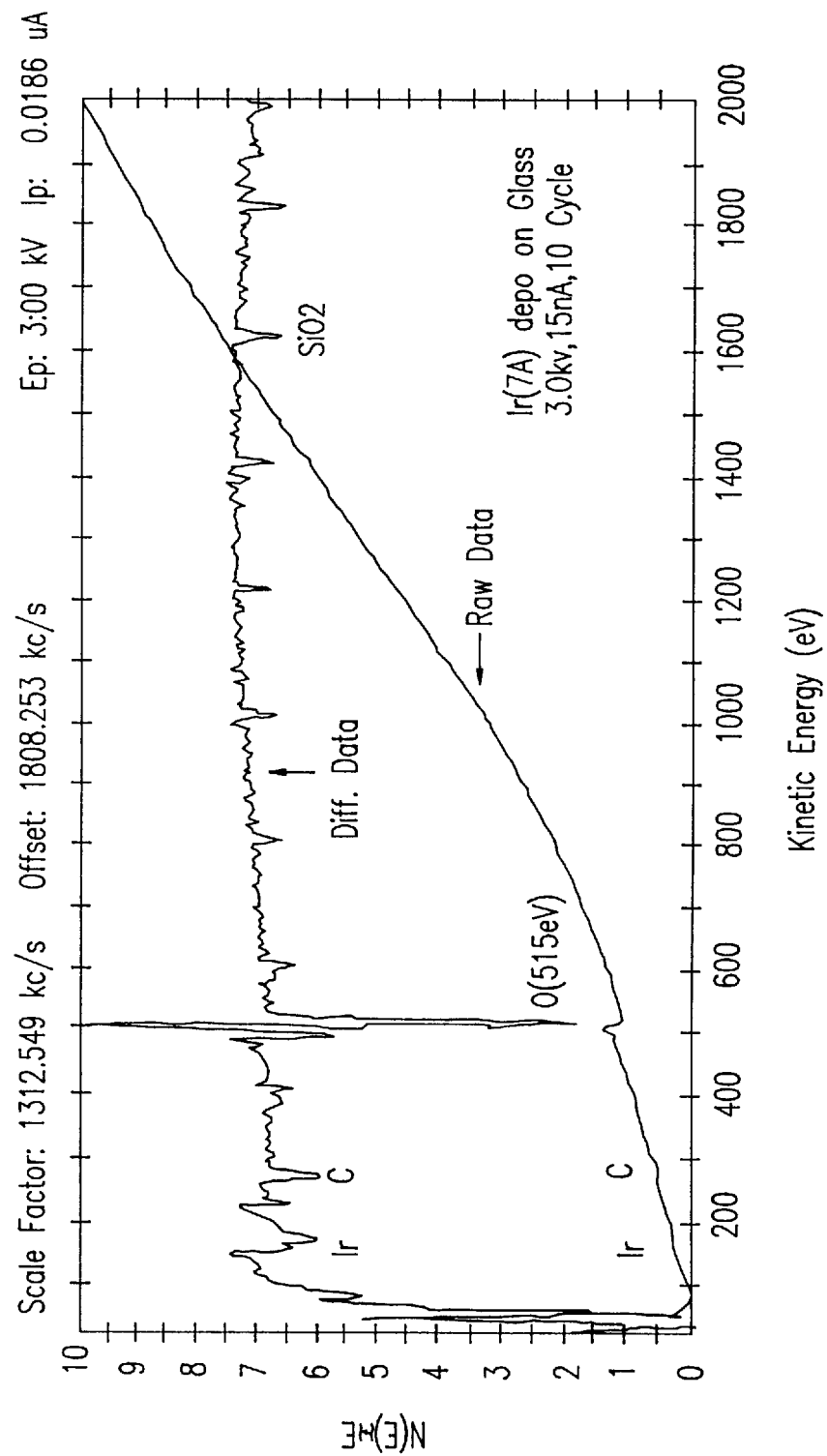
FIG. 6 is a graph of an AES analysis where an iridium layer formed on glass has a thickness of 7 Å and uses a beam voltage of 3 KV.
Figure 7:
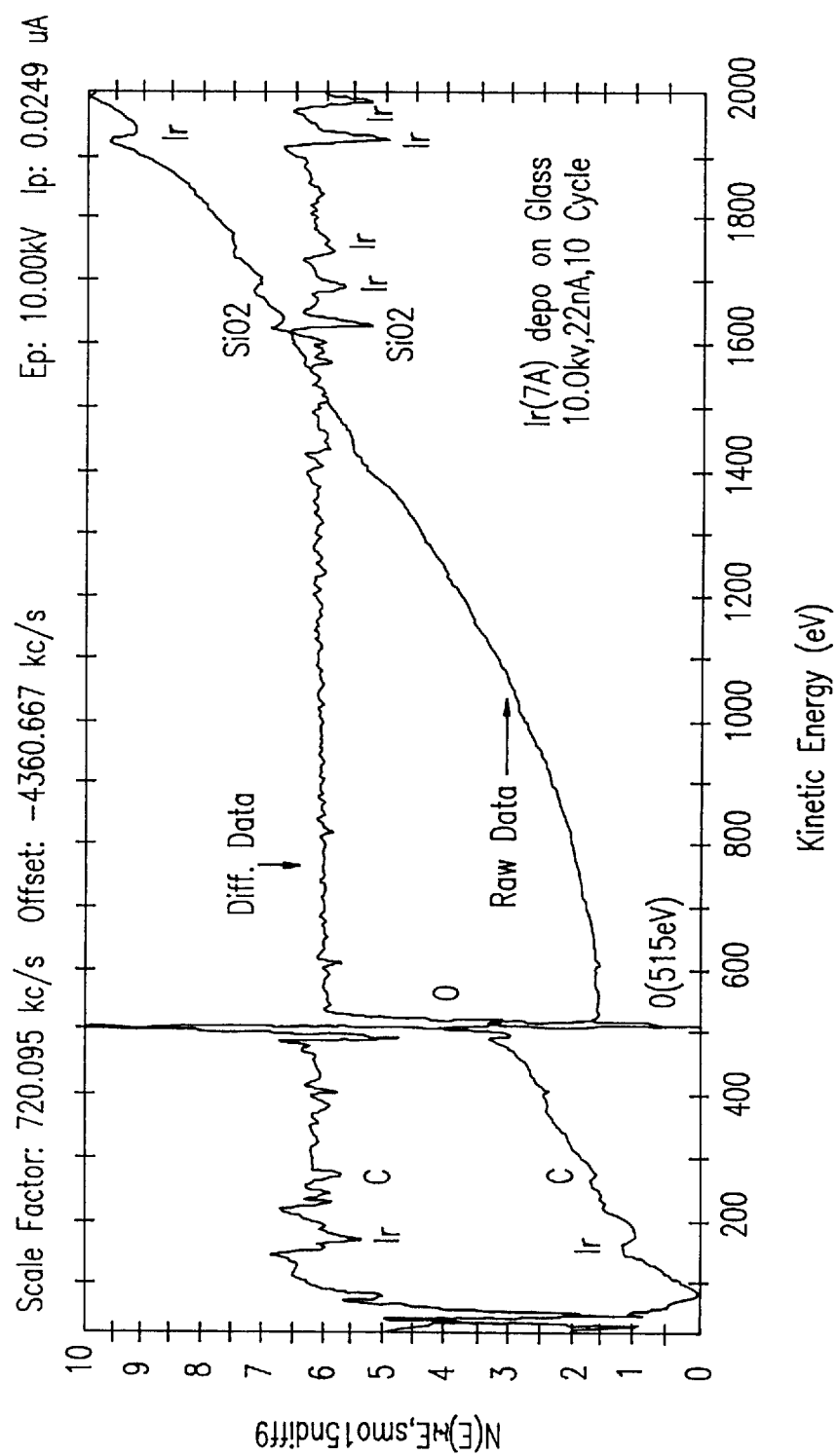
FIG. 7 is a graph of an AES analysis where an iridium layer formed on glass has a thickness of 7 Å and uses a beam voltage of 10 KV.
Figure 8:
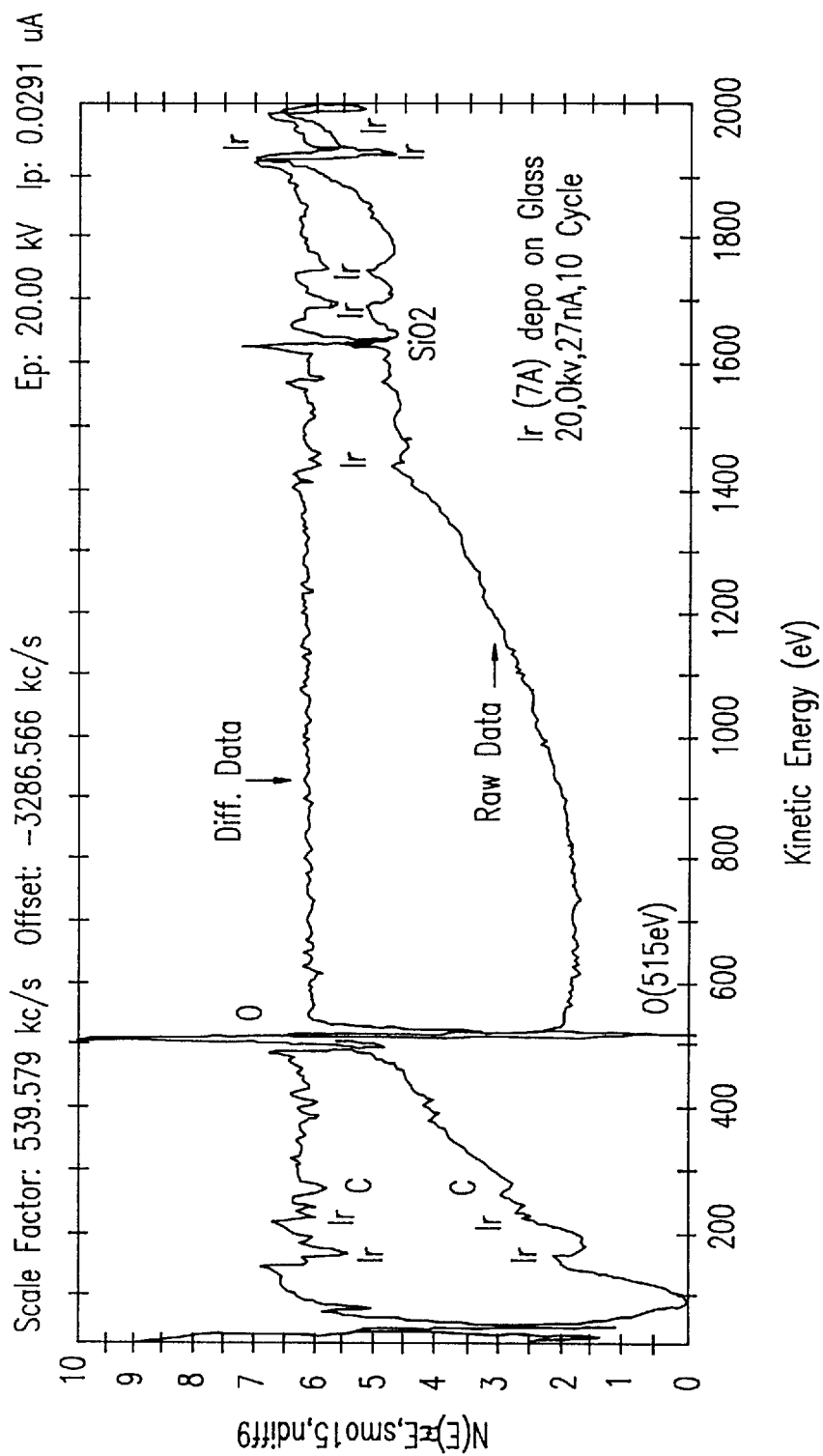
FIG. 8 is a graph of an AES analysis where an iridium layer formed on glass has a thickness of 7 Å and uses a beam voltage of 20 KV.

FIG. 2 is a graph of the AES analysis where the iridium layer has a thickness of 3 Å and the beam voltage is 3 KV. FIG. 3, FIG. 4 and FIG. 5 are graphs of the AES analyses where the iridium layer has a thickness of 5 Å and beam voltages are 3 KV, 10 KV and 20 KV, respectively. FIG. 6, FIG. 7 and FIG. 8 are graphs of the AES analyses where the iridium layer has a thickness of 7 Å and beam voltages are 3 KV, 10 KV and 20 KV, respectively.

The Raw Data denoted in FIGS. 2 through 8 are measured with the AES device and actually displayed, the raw data values being converted so as to be easily analyzed and displayed as Diff Data.

TABLE 1

Experimental Results for Controlling Charge Accumulation According to the Thickness of the Conductive Layer and Beam Voltage

| Beam Voltage | Thickness | | |
|---|---|---|---|
| | 3Å | 5Å | 7Å |
| 3 KV | cannot analyze due to charge accumulation | increasing charge accumulation noise; can analyze main component | charged chemical transition; can analyze main component |
| 10 KV | cannot analyze due to charge accumulation | increasing charge accumulation noise; can analyze main component | no charge accumulation |
| 20 KV | cannot analyze due to charge accumulation | charged chemical transition; can analyze main component | no charge accumulation |

As shown in Table 1, noise due to charge accumulation and chemical transition does not occur when the conductive layer has a thickness of at least 7 Å. Additionally, charge accumulation effects decrease as the beam voltage of the AES increases, which is due to increasing amounts of secondarily generated electrons.

The subject noise is derived from the false detection of kinetic energy in a certain frequency band due to the release of auger electrons so that the effects of charge accumulation are not completely removed. Chemical transitions result from the accumulation of total kinetic energy due to charge accumulation.

It is possible to analyze some elements to a certain degree under less than optimum conditions, but, as shown in Table 1 and FIG. 2 through FIG. 8, a highly successful AES analysis is attained when the thickness of a conductive layer is at least 7 Å and a beam voltage is over 10 KV.

A preferred embodiment of the present invention applies iridium as the material for forming the conductive layer. But, other conductive materials such as chrome and gold that are not components included in a sample may also be successfully used.

According to the present invention, the AES analytical method makes it possible to precisely analyze the surface of insulating samples, such that reliable data from the AES analysis can be obtained for general semiconductor samples.

While a preferred embodiment of the present invention has been described, it will be understood by those skilled in the art that various changes and modifications may be made, and equivalents may be substituted for elements thereof without departing from the true scope of the present invention. Therefore, it is intended that the present invention not be limited to the particular embodiment disclosed, but that the present invention include all embodiments falling within the scope of the appended claims.

What is claimed is:

1. A method of Auger Electron Spectroscopic (AES) analysis for a sample having an insulating layer formed thereon, said method comprising the steps of:

(a) depositing a conductive layer of a designated thickness on a surface of said insulating layer, wherein said designated thickness is in a range of at least about 6 Å to about 50 Å;

(b) drawing an electric charge from said surface of said insulating layer through said conductive layer to prevent charge accumulation in said insulating layer; and (c) carrying out the AES analysis of said sample.

2. The method as claimed in claim 1, said step (c) comprising a sub-step of applying a beam voltage of at least 3 Kev.

3. The method as claimed in claim 1, wherein said conductive layer is made of iridium(Ir).

4. The method as claimed in claim 1, wherein said conductive layer is made of chrome(Cr).

5. The method as claimed in claim 1, wherein said conductive layer is made of gold(Au).

6. The method as claimed in claim 1, wherein said step (a) is carried out using ion beam sputtering.

7. The method as claimed in claim 1, wherein said sample is glass used for an LCD.

8. The method as claimed in claim 1, said step (c) comprising a sub-step of applying a beam voltage of at least 10 Kev.

9. The method as claimed in claim 8, wherein said designated thickness is 7 Å.

* * * * *